(12) United States Patent
Woolley

(10) Patent No.: US 7,186,226 B2
(45) Date of Patent: Mar. 6, 2007

(54) PROCESS FOR MAKING A MASSAGE DEVICE DEPARTING FROM AN ELECTRIC TOOTHBRUSH

(76) Inventor: Graham Woolley, East Wing, Farley Castle, Farley Hill, Berkshire RG7 1XD (GB)

(*) Notice: Subject to any disclaimer, the term of this patent is extended or adjusted under 35 U.S.C. 154(b) by 194 days.

(21) Appl. No.: 10/503,268

(22) PCT Filed: Feb. 7, 2003

(86) PCT No.: PCT/EP03/01239

§ 371 (c)(1),
(2), (4) Date: Aug. 2, 2004

(87) PCT Pub. No.: WO03/068130

PCT Pub. Date: Aug. 21, 2003

(65) Prior Publication Data

US 2005/0159686 A1    Jul. 21, 2005

(30) Foreign Application Priority Data

Feb. 12, 2002  (GB) .................. 0203234.0
Oct. 23, 2002  (GB) .................. 0224584.3

(51) Int. Cl.
*A61H 1/00*  (2006.01)

(52) U.S. Cl. .................. 601/46; 601/137; 601/138

(58) Field of Classification Search ............ 601/46, 601/137–142
See application file for complete search history.

(56) References Cited

U.S. PATENT DOCUMENTS

| 3,183,538 | A | | 5/1965 | Hobner |
| 3,375,381 | A | | 3/1968 | Tavel |
| 3,941,424 | A | * | 3/1976 | Balamuth et al. ............. 300/21 |
| 4,344,202 | A | | 8/1982 | Hayat |
| 4,827,551 | A | | 5/1989 | Maser et al. |
| 5,863,102 | A | * | 1/1999 | Waguespack et al. ......... 300/11 |

FOREIGN PATENT DOCUMENTS

| DE | 25 00 132 A | 7/1976 |
| DE | 3241094 A1 | 5/1984 |
| DE | 200 07 463 U1 | 10/2000 |
| EP | 0 744 139 A1 | 11/1996 |
| GB | 1021836 | 3/1966 |
| GB | 1 293 876 | 10/1972 |
| GB | 2 375 050 A | 11/2002 |
| WO | WO-01/28452 A | 4/2001 |

* cited by examiner

*Primary Examiner*—Michael A. Brown
(74) *Attorney, Agent, or Firm*—Birch, Stewart, Kolasch, & Birch, LLP.

(57) ABSTRACT

There is provided a process for making a massage device comprising taking the body and motor of an electric toothbrush and a brush head therefor; and adapting the bristle head of said brush head to produce a massage head that is substantially smooth and devoid of bristles.

11 Claims, 6 Drawing Sheets

PROCESS FOR MAKING A MASSAGE DEVICE DEPARTING FROM AN ELECTRIC TOOTHBRUSH

FIELD OF THE INVENTION

The present invention relates to a process for making a massage device and accessories therefor. In particular, the present invention relates to a process for making a massage device for sexual stimulation.

DESCRIPTION OF THE BACKGROUND ART

The sex toy marketplace is dominated by cheap, poorly manufactured and largely ineffective vibrators and clitoral stimulators. Clitoral or "G"-spot stimulators are usually underpowered and ineffective. The stimulators on the market that have proven effective are usually mains powered and expensive.

Electric toothbrushes are known for their stimulating vibrations. However, such devices are not designed nor are they suited for use as sexual massage devices.

Electric toothbrushes are becoming increasingly common in homes and are widely available as an affordable luxury, even necessity.

BRIEF SUMMARY OF THE INVENTION

It is therefore an object of the present invention to provide a process for making a massage device that can use the motor component and body of a commonplace electric toothbrush. Another object of the present invention is to provide a process for making low cost and lightweight massage heads for use with the massage device mentioned supra. Yet a further object of the present invention is to provide a process for making a sexual massage device that is small and discrete; the appearance of most sex toys is usually very indicative of their purpose which can be embarrassing for owners and users.

According to one aspect of the present invention there is provided a process for making a massage device comprising
(a) taking the body and motor of an electric toothbrush and a brush head therefor, said brush head comprising a bristle head; and
(b) adapting said bristle head to produce a massage head that is substantially smooth and devoid of bristles.

As used herein, the term substantially smooth is defined as a surface, that is not rough, sharp or abrasive and may include a surface which contains shallow protuberances such as ridges, ribs or mounds.

As used herein, the term brush head is used to mean that part of the electric toothbrush which comprises a bristle head, typically located at one end of a shaft. The shaft itself, typically connects at its other end to the body and motor of the electric toothbrush. The bristle head typically comprises a base shaped for receipt of plural bristles and plural bristles received thereby. The bristle head is typically provided with a mounting for mounting the bristle head to the brush head of the electric toothbrush. In turn, the brush head is mountable to the body and motor of the electric toothbrush.

The adaptation of the bristle head can be achieved in a variety of ways.

In a first aspect, the bristles of the bristle head are trimmed (typically to a length of less than 1 mm, preferably less than 0.5 mm) or the bristles are pulled out entirely (e.g. using pliers). A resin is then applied to the remaining bristle head (generally in the same area as the trimmed bristles) to form the smooth massage head. Typically, the resin is an epoxy resin. Desirably, from a production standpoint the resin is quick setting.

Epoxy resin is particularly suitable because it beads well and forms a very strong bond with the remaining bristle head. The quantity and viscosity of the resin used will determine the final shape of the smooth massage head. From a production point of view, UV setting epoxy resins are suitable. The epoxy resin used must be of a medical grade suitable for the intended purpose, and for all other possible uses.

In a second aspect, the bristles of the bristle head are again trimmed (typically to a length of less than 1 mm, preferably less than 0.5 mm) or the bristles are pulled out entirely (e.g. using pliers). A smooth massage head fixture is then applied to the remaining bristle head (generally in the same area as the trimmed bristles) to form the smooth massage head.

In a first variation of the second aspect, the smooth massage head fixture is adhesively fixed to the remaining bristle head.

In a second variation of the second aspect, the smooth massage head fixture is shaped to engage with the remaining bristle head. In one example, the massage head fixture is provided with a collar which is shaped to engage the remaining bristle head.

Once engaged, the massage head fixture and remaining bristle head may be permanently fixed by means of a bonding or welding operation. All known types of welding are suitable including heat welding and ultrasound welding. In one aspect, the weld is obtainable by energy generated by a sonitrode head, of energy output 100–200 Watts, frequency 20–50 kHz and duration 100–200 milliseconds. In one aspect, the weld is a single continuous weld. In another aspect, the weld comprises a plurality of spot welds such as from 2 to 100, more preferably 4 to 50 spot-welds.

In a third aspect, the bristles of the bristle head are again trimmed (typically to a length of less than 1 mm, preferably less than 0.5 mm). The remaining bristle head is then smoothed by a mechanical smoothing process (e.g. an abrasive smoothing process) to form the smooth massage head.

In a fourth aspect, the bristles are pulled out of the bristle head. Optionally, and when required, the remaining bristle head is (further) smoothed by a mechanical smoothing process to form the substantially smooth massage head. Suitably, the pulling out is achieved by initially using a gripping means to grip the ends of the bristles and then applying pulling force to pull the bristles from the bristle head. In one particular aspect, a set of pliers is used to pull the bristles from the bristle head.

According to another aspect of the present invention there is provided a process for making a massage device comprising
(a) taking the body and motor of an electric toothbrush and a brush head therefor, said brush head comprising a bristle head; and
(b) replacing said bristle head with a massage head that is substantially smooth and devoid of bristles.

The massage head may comprise a component made from rubber, plastics, metal, wood or fabric. The head may be smooth or it may be textured.

The motor of the electric toothbrush may be mains powered and/or have a rechargeable power source.

One or more batteries may power the motor of the electric toothbrush.

The motor of the electric toothbrush may provide vibrational and/or rotational movement and/or oscillatory movement and/or combinations thereof.

Alternatively or in addition, the motor of the electric toothbrush may provide translation movement.

In one aspect, the motor of the electric toothbrush may provide continuous movement. In another aspect, the motor of the electric toothbrush provides pulsed movement.

In one aspect, the massage device may further comprise an intermediate shaft for positioning between the body of the electric toothbrush and the massage head. In this aspect, the intermediate shaft may convert the movement generated by the motor of the electric toothbrush from one mode to another.

Alternatively or in addition, the intermediate shaft may convert the movement from rotational movement to vibrational movement and/or translational movement and/or oscillatory movement.

In one aspect, the massage head may convert the movement generated by the motor of the electric toothbrush from one mode to another, for example, may convert the movement from rotational movement to vibrational movement and/or translational movement and/or oscillatory movement.

The massage device herein may be provided as a kit of parts comprising a body and a motor of an electric toothbrush; a massage head, said head being substantially smooth and devoid of bristles. Suitably, the kit further comprises a power source.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description

BRIEF DESCRIPTION OF THE DRAWINGS

The invention will now be described further with reference to the accompanying drawings which are given by way of illustration only, and thus are not limitative of the present invention, and in which.

DETAILED DESCRIPTION OF THE INVENTION

Figure 1:
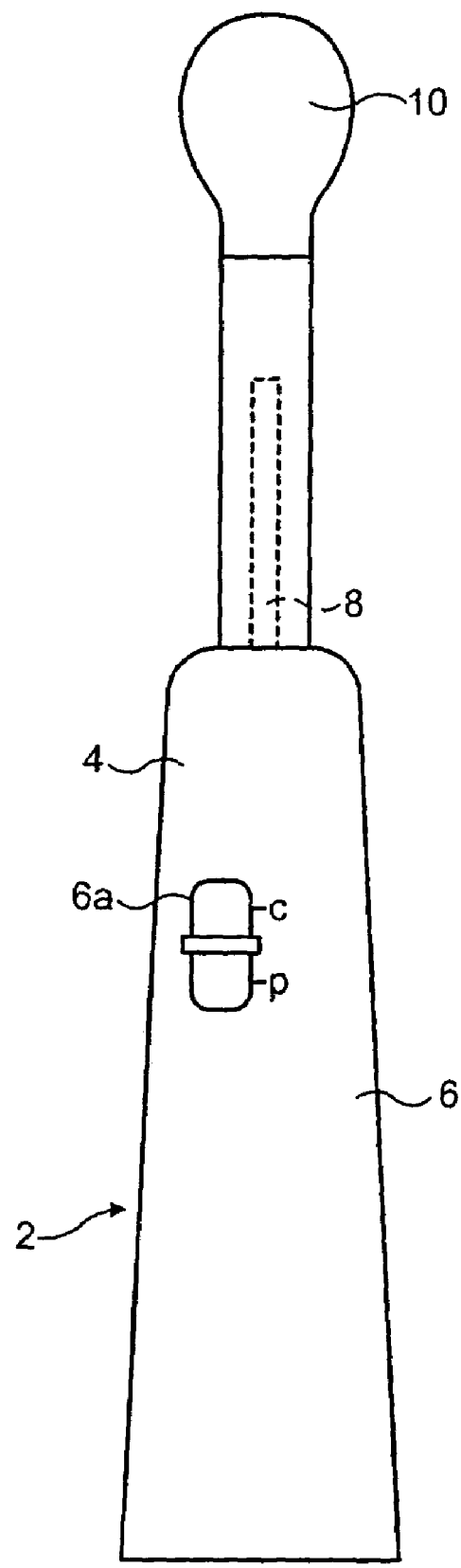
FIG. 1 shows a side view of a massage device obtainable by the process in accord with the present invention.

Referring now to the figures, FIG. 1 illustrates a massage device 2 comprising a motor (not shown) and a body 4 of a commonplace standard electric toothbrush. The body 4 takes the form of an elongate handle 6 and a shaft 8 on which a regular electric toothbrush head may be applied. In the present invention, the toothbrush head is replaced with a massage head 10. The body 4 contains a control 6a for choosing between continuous or pulsed motor action.

In this embodiment, the head contains a mechanical mechanism to convert the rotation provided by the motor of the electric toothbrush body 4 into back-and-forward and/or vibrational movement of the head. In contrast to a device wherein the entire device is vibrating, in the present invention, the energy from the device is directed and concentrated at the point at which the head is applied.

Figure 2:
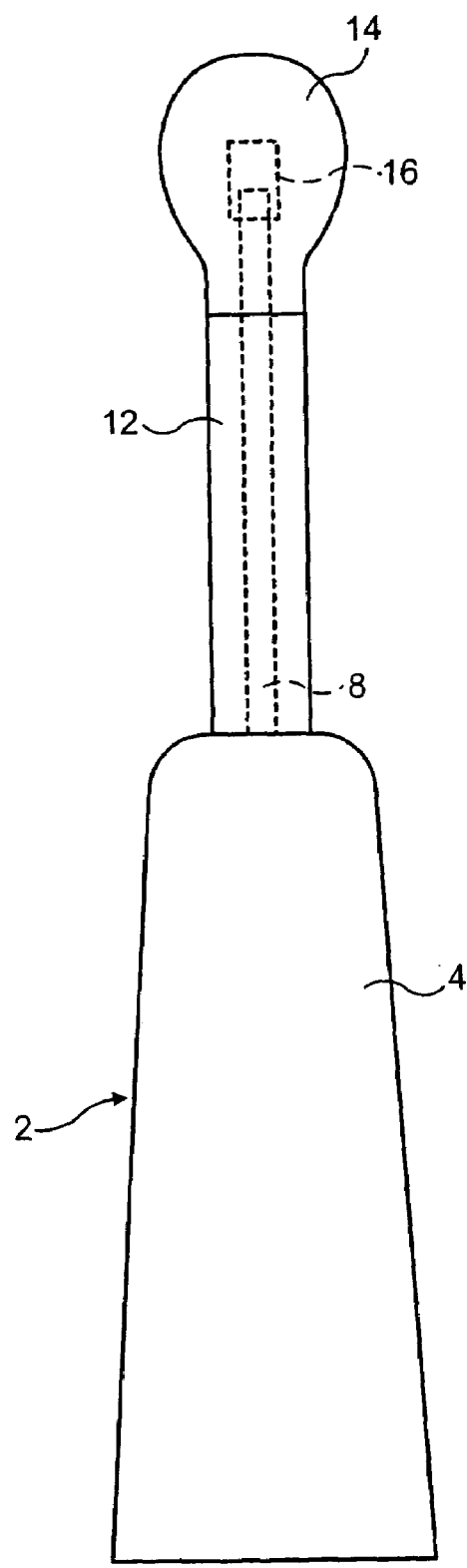
FIG. 2 shows a side view of a massage device comprising an intermediate shaft and remote massage head also obtainable by the process in accord with another aspect of the invention.

In FIG. 2, the massage device 2 has an intermediate neck 12 linked to the body 4 and a remote massage head 14. The intermediate neck 12 remains stationary during use and transmits the forces produced by the motor and rotating shaft 8 to the remote head 14 via a head agitation mechanism 16 (shown in outline).

Figure 3:
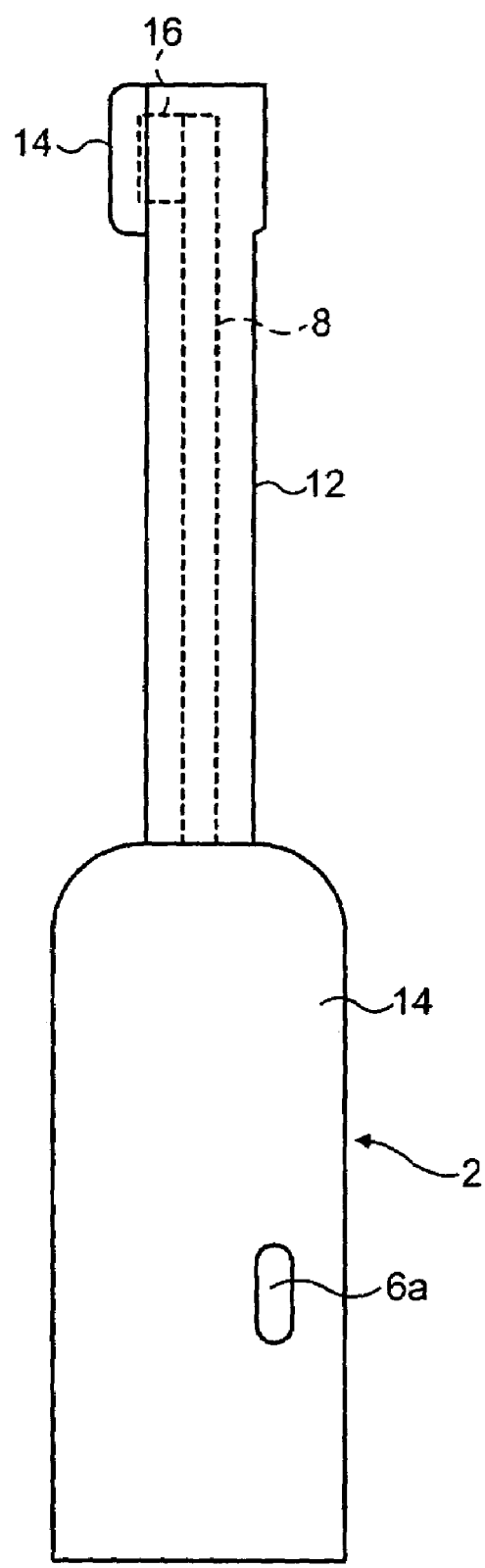
FIG. 3 shows a massage device comprising an intermediate shaft and smooth circular remote massage head further obtainable by the process in accord with another aspect of the invention.

In FIG. 3, the massage device 2 also has an intermediate neck 12 linked to the body 4 and a remote massage head 14. The intermediate neck 12 remains stationary during use and transmits the forces produced by the motor and rotating shaft 8 to the smooth circular head 14 via a head agitation mechanism 16 (shown in outline). The body 4 contains a simple on/off control 6a.

Figure 4:
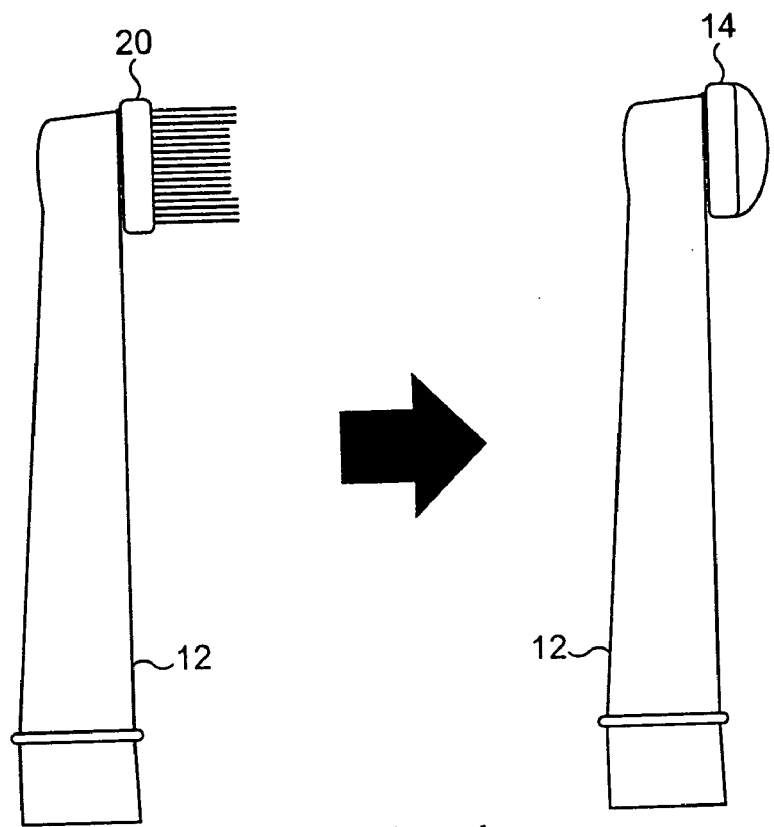
FIG. 4 shows the outline of a process in accord with the present invention.

FIG. 4 shows in outline a process aspect herein. An electric toothbrush head comprising an intermediate neck 12 and remote bristle head 20 is shown both in unadapted form (left hand view) and then in adapted form (right hand view) in which in place of the bristle head 20 there is provided smooth massage head 14.

Figure 5:
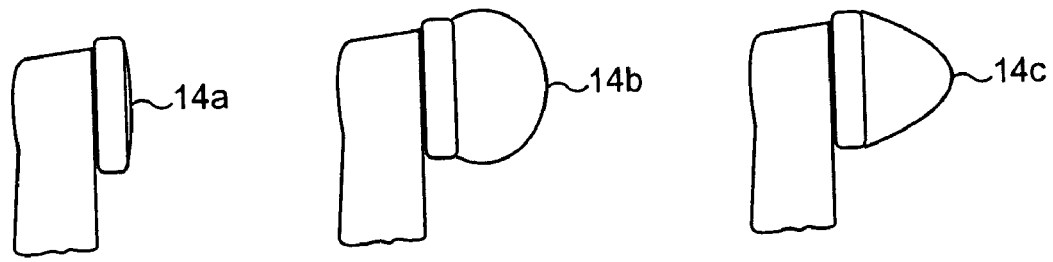
FIG. 5 shows three alternative smooth massage head shapes for use in accord with the present invention.

FIG. 5 shows three alternative smooth massage head shapes. The alternatives are (from left to right) flat-headed 14a; bulb-headed 14b; and pointed-headed 14c.

Figure 6:
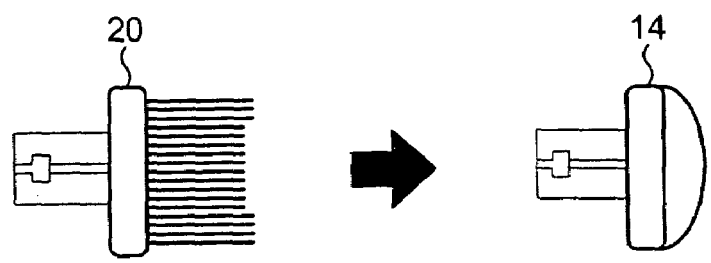
FIG. 6 shows the outline of a first process in accord with the present invention.

FIG. 6 shows in outline a process aspect herein. The remote bristle head 20 of an electric toothbrush head is simply replaced by a remote smooth massage head 14. It may be appreciated that either head 14, 20 is suitable for mounting to the intermediate neck 12 of a toothbrush or massage head as shown in FIG. 4.

The advantage of the simple replacement process of FIG. 6 is that it only involves creating new tooling for one modified part (i.e. the smooth massage head 14) to replace the bristle head 20. Every other part of the electric toothbrush can remain unchanged. This represents a very low cost solution for toothbrush head manufacturers.

The method of FIG. 6 can also be adapted to make it difficult for competing manufacturers as it first involves removing the existing bristle head part. This is usually difficult to do without damaging the original toothbrush head. Additionally, although there is only one replacement part, it is usually quite a complex small plastic part, often with a small metal bearing.

Figure 7:
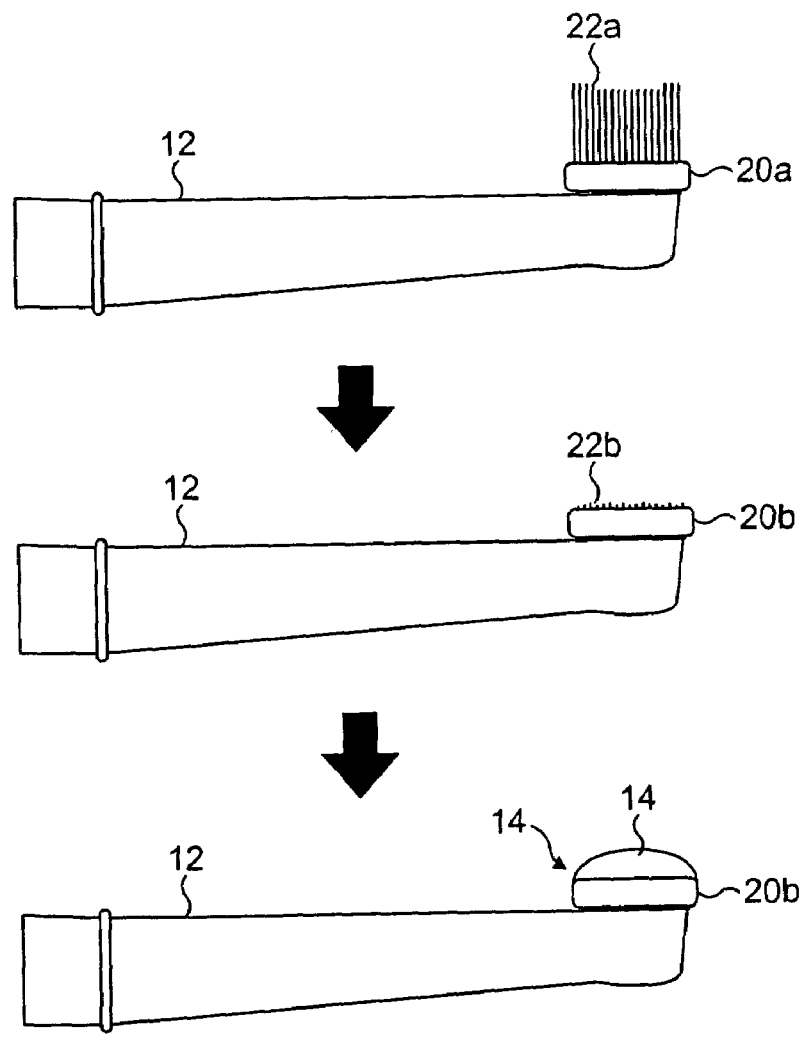
FIG. 7 shows the outline of a second process in accord with the present invention.

FIG. 7 shows an alternative process herein. An electric toothbrush head comprising an intermediate neck 12 and remote bristle head 20a is first taken. The bristles 22a of the bristle head 20a are significantly trimmed down (e.g. by cutting) to produce a trimmed bristle head 20b in which the bristles are typically of a length of no more than 1 mm. In one variation herein, the trimming down step is replaced by a step in which the bristles are physically pulled out of the bristle head 20a such as by the action of a pair of pliers. A smooth massage head 14 is then created by applying a small amount of epoxy resin to the trimmed bristle head 20b and shaping the so applied resin to form the head tip 14.

Epoxy resin is used because it beads well and forms a very strong bond with the remaining bristle 20b base. The quantity and viscosity of the resin used will determine the final shape of the rounded head 14. From a production point of view, UV setting epoxy resins are suitable.

The epoxy resin method is well suited to third-party modification of existing toothbrush heads. Initial investment is low, and the method involves a simple manufacturing techniques. These advantages also apply to the process shown in FIG. 8.

Figure 8:
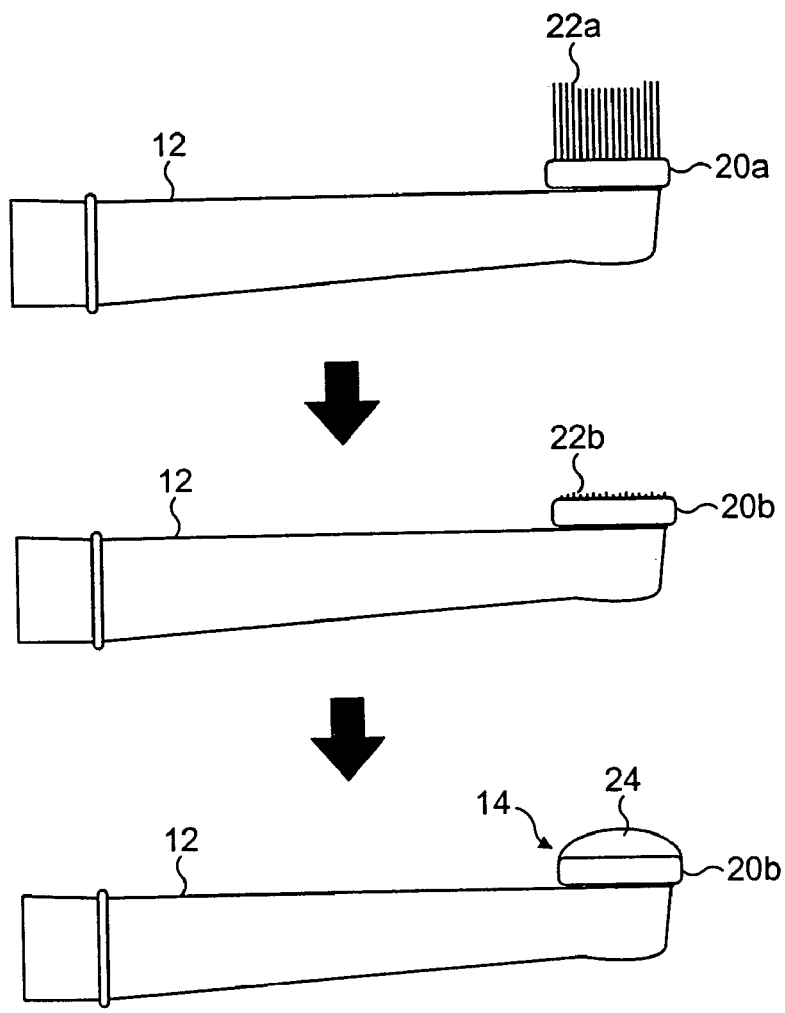
FIG. 8 shows the outline of a third process in accord with the present invention.
Figure 9:
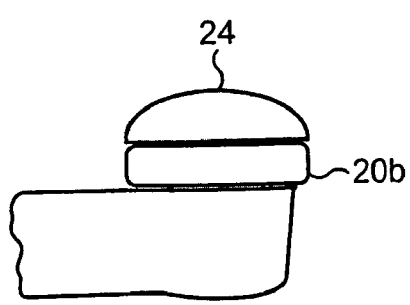
FIGS. 9 and 10 show alternative aspects of the process of FIG. 8.
Figure 10:
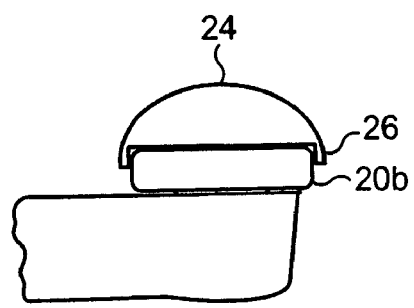

FIG. 8 shows an alternative process, which however has its first two steps in common with those of FIG. 7. That is to say: An electric toothbrush head comprising an intermediate neck 12 and remote bristle head 20a is first taken. The bristles 22a of the bristle head 20a are significantly trimmed down (e.g. by cutting) to produce a trimmed bristle head 20b in which the bristles are typically of a length of no more than 1 mm. In the process of FIG. 8 however, the smooth massage head 14 is created by capping the trimmed bristle head 20b with a smooth massage head cap 24 to form a smooth massage head 14. FIGS. 9 and 10 show alternative ways of securing the smooth massage head cap 24 to the trimmed bristle head 20b. As in FIG. 7, the trimming down step may in aspects, be replaced by a step in which the bristles are physically pulled out of the bristle head.

In the process of FIG. 9, the smooth massage head cap 24 is adhesively fixed flush to the trimmed bristle head 20b. In the process of FIG. 10, the smooth massage cap 24 is provided with a collar 26, which engages the trimmed bristle head 20b and the so engaged parts are welded together (i.e. trimmed bristle head 20b to collar 26).

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. A process for making a massage device comprising
   (a) taking the body and motor of an electric toothbrush and a brush head therefor, said brush head comprising a bristle head; and
   (b) adapting said bristle head to produce a massage head that is substantially smooth and devoid of bristles,
   wherein the bristles of the bristle head are trimmed or pulled out and a resin applied to the remaining bristle head to form the substantially smooth massage head.

2. The process according to claim 1, wherein the resin is an epoxy resin.

3. The process according to claim 2, wherein the epoxy resin is a UV setting epoxy resin.

4. A process for making a massage device comprising
   (a) taking the body and motor of an electric toothbrush and a brush head therefor, said brush head comprising a bristle head; and
   (b) adapting said bristle head to produce a massage head that is substantially smooth and devoid of bristles,
   wherein the bristles of the bristle head are trimmed or pulled out and a smooth massage head fixture applied to the remaining bristle head to form the substantially smooth massage head.

5. The process according to claim 4, wherein the smooth massage head fixture is adhesively fixed to the remaining bristle head.

6. The process according to claim 4, wherein the smooth massage head fixture is shaped to engage with the remaining bristle head.

7. The process according to claim 6, wherein the massage head fixture is provided with a collar for engagement with the remaining bristle head.

8. The process according to claim 6, wherein once engaged, the massage head fixture and the remaining bristle head are permanently fixed by means of a bonding or welding operation.

9. The process according to claim 7, wherein once engaged, the massage head fixture and the remaining bristle head are permanently fixed by means of a bonding or welding operation.

10. A process for making a massage device comprising
    (a) taking the body and motor of an electric toothbrush and a brush head therefor, said brush head comprising a bristle head; and
    (b) adapting said bristle head to produce a massage head that is substantially smooth and devoid of bristles,
    wherein the bristles of the bristle head are trimmed and the remaining bristle head is smoothed by a mechanical smoothing process to form the substantially smooth massage head.

11. A process for making a massage device comprising
    (a) taking the body and motor of an electric toothbrush and a brush head therefor, said brush head comprising a bristle head; and
    (b) adapting said bristle head to produce a massage head that is substantially smooth and devoid of bristles,
    wherein the bristles are pulled out of the bristle head and optionally, the remaining bristle head is smoothed by a mechanical smoothing process to form the substantially smooth massage head.

* * * * *